United States Patent
Godfrey

(12) 
(10) Patent No.: US 6,345,983 B1
(45) Date of Patent: Feb. 12, 2002

(54) DENTIST'S FORCEPS

(76) Inventor: Duane K. Godfrey, 3255 Western Ave., Idaho Falls, ID (US) 83406

( * ) Notice: Subject to any disclaimer, the term of this patent is extended or adjusted under 35 U.S.C. 154(b) by 0 days.

(21) Appl. No.: 09/861,115

(22) Filed: May 18, 2001

(51) Int. Cl.[7] .................................................. A61C 3/14
(52) U.S. Cl. ..................................................... 433/159
(58) Field of Search ............................... 433/159, 160, 433/4, 39

(56) References Cited

U.S. PATENT DOCUMENTS

| | | | |
|---|---|---|---|
| 315,706 A | 4/1885 | Brewer et al. | 433/159 |
| 388,619 A | 8/1888 | Booth | 433/159 |
| 1,143,927 A | 6/1915 | Allen | 433/159 |
| 5,197,877 A | 3/1993 | Andrew | 433/153 |
| 5,257,558 A | 11/1993 | Frazin-Nia et al. | 433/159 |
| 5,947,731 A | 9/1999 | Fell | 433/159 |
| 5,993,210 A | 11/1999 | Godfrey | 433/159 |

FOREIGN PATENT DOCUMENTS

DE  3436-147 A  4/1986

*Primary Examiner*—John J. Wilson

(57) ABSTRACT

A scissor-like device having narrow jaws and a sliding rectangular closing clamp between the two handle halves that operates like a hemostat, i.e., it maintains the jaws in a fixed position. The jaw tips are oval-shaped to pry the teeth and matrix band slightly apart during the filling procedure. Closing the handle separates two teeth and the matrix band from a center tooth. The jaws have a diamond abrasive coating for gripping an inner surface of the matrix band.

3 Claims, 2 Drawing Sheets

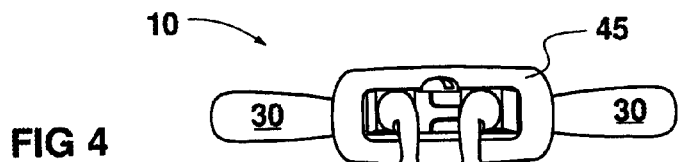
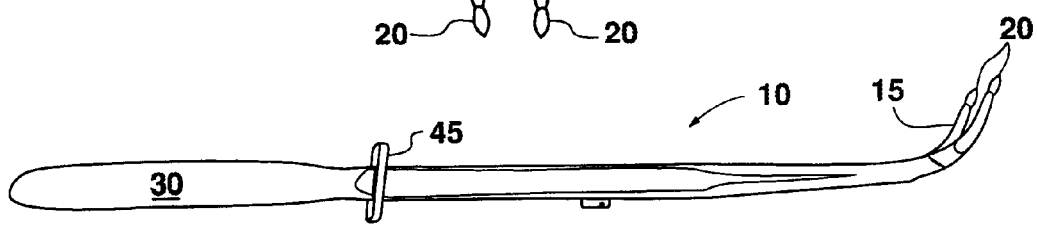
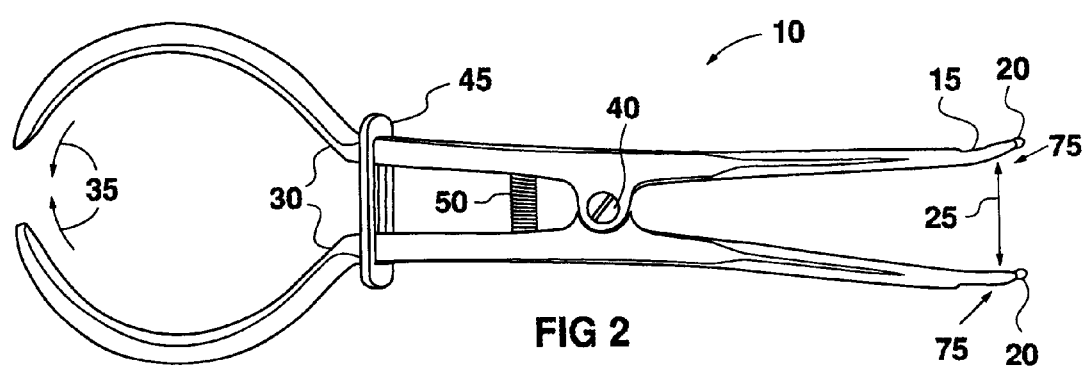
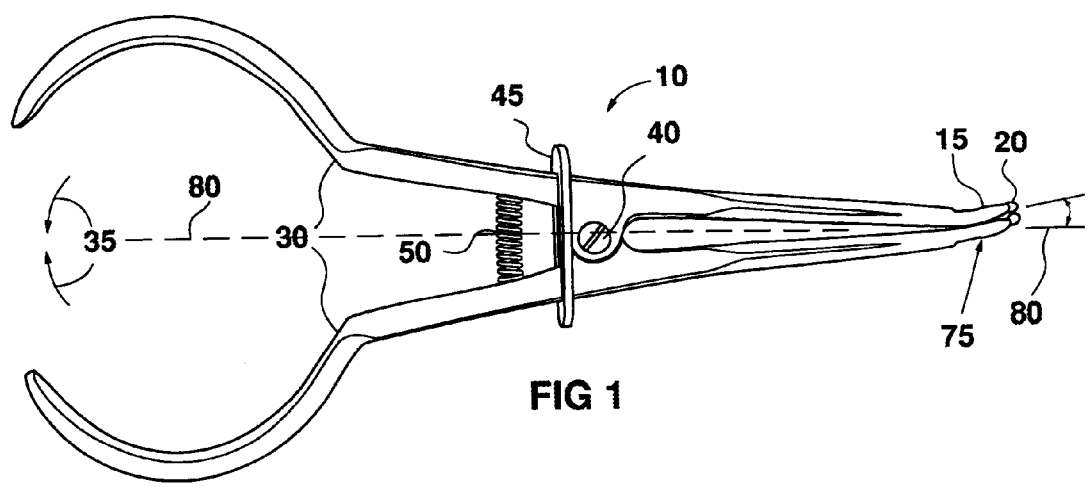

DENTIST'S FORCEPS

TECHNICAL FIELD

This invention relates in general to a dentist's forceps that can be used to separate two teeth from a central third tooth during a dental tooth filling procedure. Additionally, the forceps exert a force on an inner surface of a metal matrix surrounding the central tooth.

BACKGROUND OF THE INVENTION

In dental filling procedures for molars and premolars, a metal matrix band is placed around the tooth to be worked on. It is desirable to slightly separate the one or two adjacent teeth (one in front and one behind) depending on the size of the filling. If the filling is on a forward portion of the tooth, only the forward adjacent tooth needs to be separated from the matrix banded tooth. If the filling goes from front to back of the tooth, both adjacent teeth need to be slightly separated from the affected tooth.

The reason for the separation during the filling process is to allow the adjacent teeth to move towards the filled tooth after the filling is completed to close up the gap. This prevents food particles from being lodged in the space between the filled tooth and adjacent teeth.

It is important during this filling process that the separation device or forceps be in close and slip-proof contact with the somewhat slippery stainless steel metal band or matrix that surrounds this central tooth. The forceps must hold the matrix fixed during the resin filling of the tooth and for the curing time after resin fill.

Tooth separators that have been in use include movable wedge shapes, threaded clamps, wedges and other mechanical devices.

It is the purpose of this invention to provide an infinitely adjustable dentist's forceps that maintains a fixed separation between one or more teeth and provides a constant slip-proof grip on the metal matrix during the filling procedure.

SUMMARY OF THE INVENTION

The forceps consist of a scissor-like device having oval diamond dust jaws and a sliding rectangular clamp on the two handle halves that operates to maintain the jaws in a fixed position. The jaws are oval-shaped to match the contour of central tooth being filled. The jaws have the diamond dust coating to enhance a grip on a metal matrix.

Specifically, the dentist's forceps consist of a pair of arcuate jaws; a pair of handle halves attaching to the jaws; a center pivot pin connecting the pair of handle halves; and a sliding rectangular clamp wherein when the handle halves are in a closed position, the rectangular clamp maintains a fixed position of the arcuate jaws.

BRIEF DESCRIPTION OF THE DRAWINGS

FIG. 1 is a top view of the dentist's forceps in the closed, unlocked position.

FIG. 2 is a top view of the dentist's forceps in the open, locked position.

FIG. 3 is a side elevation of the dentist's forceps.

FIG. 4 is a front elevation of the dentist's forceps.

DETAILED DESCRIPTION OF THE INVENTION

Figure 6:
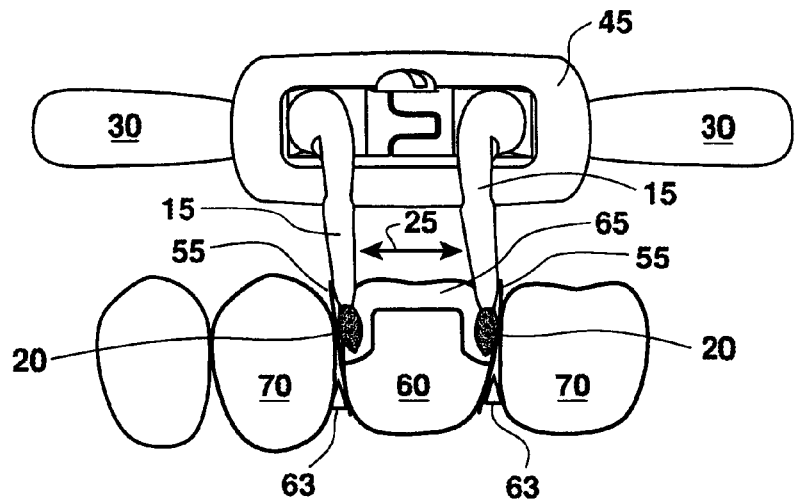
FIG. 6 is a front elevation of the dentist's forceps inserted between two teeth adjacent to the affected tooth.

FIGS. 1 through 4 illustrate a dentist's forceps 10 having a pair of arcuate jaws 15 having oval diamond-dust jaw tips 20. The jaws 15 are moved in direction of arrow 25 by squeezing handle halves 30 in direction 35. This causes the jaws 15 to separate (FIG. 2) since the handle halves 30 are attached by pivot pin 40. When the proper tooth separation is obtained, the sliding rectangular clamp 45 on the handle halves 30 maintain the jaws in a fixed open position and the handle halves 30 can be released. Compression spring 50 normally holds the jaws closed when not in use.

The diamond abrasive is coated on the jaw tips 20 to provide a maximum abrasive grip on the interior surface of a metal matrix band that surrounds the tooth during the cavity filling procedure. The jaw tips 20 are an oval shape so as to more closely match the contour of the missing surface of the affected and drilled tooth.

Figure 5:
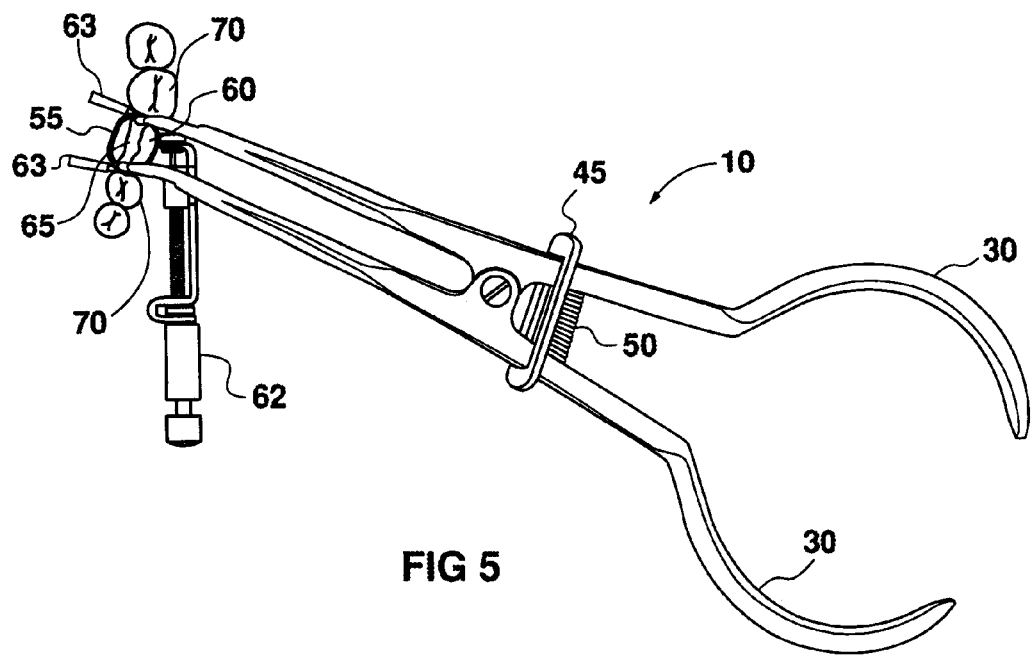
FIG. 5 is a top view of the dentist's forceps inserted between two teeth adjacent to an affected tooth.

FIGS. 5 and 6 illustrate the use of forceps 10 while filling a tooth cavity. The diamond abrasive jaw tips 20 are bearing against an interior surface of the metal matrix band 55. The matrix band 55 is tightened around tooth 60 by a Tofflemire matrix holder 62 and two separator wedges 63.

In FIGS. 5 and 6, the jaw tips 20 are inserted within the drilled out tooth cavity 65 and bear outwardly in direction of arrow 25 to separate the adjacent teeth 70 and provide a rounded bearing surface that simulates tooth contour, on the matrix band 55 inner surface. This contour is maintained while the cavity filling resin dries and then the hole that remains after the jaws 20 are removed is filled with additional resin. The jaws are held in position for drying by sliding rectangular clamp 45 toward the handle halves 30, as seen in FIG. 5. It should be noted that the jaws 15 are slightly bent away from centerline 80 in FIG. 1 at arrow 75 which permits better lighting and vision from above when the forceps are in use.

While the present invention has been described by reference to specific embodiments, it will be apparent that other alternative embodiments and methods of implementation or modification may be employed without departing from the true spirit and scope of the invention.

What is claimed is:

1. A dentist's forceps for use with a matrix band, the forceps comprising:

a) a pair of arcuate jaws having diamond-coated oval jaw tips;

b) a pair of handle halves having an open and closed position, said handle halves attaching to the jaws;

c) a center pivot pin connecting the pair of handle halves; and d) a sliding rectangular clamp wherein when the handle halves are in a closed position, the clamp maintains a fixed position of the arcuate jaws, and wherein the closed position of the handle halves compresses the jaw tips against an inner surface of the matrix band thereby separating a pair of adjacent teeth from a center tooth.

2. The dentist's forceps of claim 1 wherein the arcuate jaws are bent away from a centerline of the forceps.

3. The dentist's forceps of claim 1 wherein a compression spring maintains the jaws in a closed position when the forceps are not in use.

* * * * *